US010039611B2

United States Patent
Mohika

(10) Patent No.: US 10,039,611 B2
(45) Date of Patent: *Aug. 7, 2018

(54) SYSTEM AND METHOD FOR CONTAINMENT AND ORGANIZATION OF MEDICAL WIRE

(71) Applicant: Cook Medical Technologies LLC, Bloomington, IN (US)

(72) Inventor: Brian O Mohika, Lawrence, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,829

(22) Filed: Oct. 19, 2016

(65) Prior Publication Data

US 2017/0056121 A1 Mar. 2, 2017

Related U.S. Application Data

(63) Continuation of application No. 14/512,939, filed on Oct. 13, 2014, now Pat. No. 9,499,318.

(Continued)

(51) Int. Cl.
*A61B 50/20* (2016.01)
*A61B 17/12* (2006.01)
(Continued)

(52) U.S. Cl.
CPC .......... *A61B 50/20* (2016.02); *A61B 17/1214* (2013.01); *A61B 17/28* (2013.01);
(Continued)

(58) Field of Classification Search
CPC .............. A61M 5/1418; A61M 25/002; A61M 2025/09125; Y10T 24/44274;
(Continued)

(56) References Cited

U.S. PATENT DOCUMENTS

| 3,503,397 A | 3/1970 | Fogarty et al. |
| 3,503,398 A | 3/1970 | Fogarty et al. |

(Continued)

FOREIGN PATENT DOCUMENTS

| WO | WO 00/06030 | 2/2000 |
| WO | WO 2004/066846 A1 | 8/2004 |

(Continued)

OTHER PUBLICATIONS

Medline Industries, Inc., "OR Necessities® Separate Sterile Pack Components" catalog, dated 2011, p. 25, Mundelein, IL.

(Continued)

*Primary Examiner* — Robert Sandy
(74) *Attorney, Agent, or Firm* — Brinks Gilson & Lione

(57) ABSTRACT

A system for containment and organization of medical wire features a U-shaped clamp. A first ridged and grooved clamping block is located on a clamp first side posterior end and a second ridged and grooved clamping block is located on a clamp second side posterior end. A first side compression member is located on an inside surface of a clamp first side and a second side compression member is located on an inside surface of the clamp second side. An adjustable ratcheting lock attaches the clamp first side and the clamp second side. A first finger grip is located on an outside surface of the clamp first side and a second finger grip is located on an outside surface of the clamp second side. Medical wire is placed between the first side compression member and the second side compression member then the clamp is compressed against the medical wire.

20 Claims, 3 Drawing Sheets

Related U.S. Application Data

(60) Provisional application No. 62/040,305, filed on Aug. 21, 2014.

(51) Int. Cl.
*A61M 25/00* (2006.01)
*A61M 25/09* (2006.01)
*B65D 67/02* (2006.01)
*A61B 17/28* (2006.01)

(52) U.S. Cl.
CPC .......... *A61M 25/002* (2013.01); *A61M 25/09* (2013.01); *B65D 67/02* (2013.01); *A61B 2017/2808* (2013.01); *A61M 2025/09125* (2013.01); *Y10T 24/44274* (2015.01); *Y10T 24/44538* (2015.01); *Y10T 24/44564* (2015.01); *Y10T 24/44615* (2015.01); *Y10T 24/44752* (2015.01); *Y10T 24/44906* (2015.01)

(58) Field of Classification Search
CPC ......... Y10T 24/44915; Y10T 24/44538; Y10T 24/44906; Y10T 24/44615; Y10T 24/44654; Y10T 24/44752; Y10T 24/44796; B65D 67/02; A61B 17/28; A61B 17/1214; A61B 2017/2808
See application file for complete search history.

(56) References Cited

U.S. PATENT DOCUMENTS

| | | |
|---|---|---|
| 3,604,071 A | 9/1971 | Reimels |
| 4,835,824 A | 6/1989 | Durham et al. |
| 5,022,126 A | 6/1991 | Davis |
| D333,182 S | 2/1993 | Yoshikawa |
| 5,226,892 A | 7/1993 | Boswell |
| 5,489,287 A | 2/1996 | Green et al. |
| 5,573,541 A | 11/1996 | Green et al. |
| 5,591,182 A | 1/1997 | Johnson |
| 5,944,729 A | 8/1999 | Blake |
| 6,099,539 A | 8/2000 | Howell et al. |
| 6,206,896 B1 | 4/2001 | Howell et al. |
| 6,228,104 B1 | 5/2001 | Fogarty et al. |
| 6,273,902 B1 | 8/2001 | Fogarty et al. |
| 6,293,954 B1 | 9/2001 | Fogarty et al. |
| 6,299,621 B1 | 10/2001 | Fogarty et al. |
| 6,387,106 B1 | 5/2002 | Howell et al. |
| 6,387,112 B1 | 5/2002 | Fogarty et al. |
| 6,406,485 B1 | 6/2002 | Hossain et al. |
| 6,460,231 B2 | 10/2002 | Bourgerie |
| 6,530,942 B2 | 3/2003 | Fogarty et al. |
| 6,558,408 B1 | 5/2003 | Fogarty et al. |
| 6,579,304 B1 | 6/2003 | Hart et al. |
| 6,626,922 B1 | 9/2003 | Hart et al. |
| 6,692,514 B2 | 2/2004 | Fogarty et al. |
| 6,719,766 B1 | 4/2004 | Buelna et al. |
| 6,821,284 B2 | 11/2004 | Sturtz et al. |
| 6,942,676 B2 | 9/2005 | Buelna |
| 6,989,017 B2 | 1/2006 | Howell et al. |
| 7,322,995 B2 | 1/2008 | Buckman et al. |
| 7,578,827 B2 | 8/2009 | Gadberry et al. |
| 7,780,688 B2 | 8/2010 | Sakakine et al. |
| 7,850,702 B2 | 12/2010 | Sorribes |
| 8,092,473 B2 | 1/2012 | Hart et al. |
| 8,167,252 B2 | 5/2012 | Nitsche et al. |
| 8,201,310 B1 | 6/2012 | Abdi et al. |
| 8,273,102 B2 | 9/2012 | Danitz et al. |
| 8,578,571 B2 | 11/2013 | Schmidt et al. |
| 9,499,318 B2 * | 11/2016 | Mohika .................. A61M 25/09 |
| 9,664,213 B2 * | 5/2017 | Mohika ..................... F16B 2/10 |
| 2002/0007538 A1 | 1/2002 | Bourgerie |
| 2011/0210215 A1 | 9/2011 | Nitsche et al. |
| 2011/0313437 A1* | 12/2011 | Yeh ..................... A61B 17/122 |
| | | 606/158 |
| 2013/0212844 A1 | 8/2013 | Chen |

FOREIGN PATENT DOCUMENTS

| | | |
|---|---|---|
| WO | WO 2005/048854 A2 | 6/2005 |
| WO | WO 2005/096960 A1 | 10/2005 |

OTHER PUBLICATIONS

Cook Medical Technologies LLC, "Clip", at least as early as Aug. 20, 2014, 2 pgs.
Extended European Search Report, dated Jan. 20, 2016, pp. 1-12, issued in European Patent Application No. 15180264.2-1654, European Patent Office, Munich, Germany.
Wirebots 2—YouTube, available on Jun. 29, 2016, at https://www.youtube.com/watch?v=v11Pe-MnLVV0.
Wirebots Guide to Wire Management—YouTube, available on Jun. 29, 2016, at https://www.youtube.com/watch?v=FhKBiSPILy8.

* cited by examiner

SYSTEM AND METHOD FOR CONTAINMENT AND ORGANIZATION OF MEDICAL WIRE

CROSS REFERENCE

This application is a continuation of U.S. patent application Ser. No. 14/512,939 filed Oct. 13, 2014, which claims the benefit of U.S. Provisional Patent Application No. 62/040,305 filed Aug. 21, 2014, the specifications of which are incorporated herein in their entirety by reference.

FIELD OF THE INVENTION

The present invention relates to medical devices, systems, and methods, and more specifically, medical wire devices, medical wire systems, and methods of containing and organizing medical wire.

BACKGROUND OF THE INVENTION

Wire used for medical purposes is carefully manufactured, sterilized, and sealed in a sterilized package in preparation for use. Once removed from the package, this wire can be difficult to handle and keep separate from other medical wires of a different size, especially in a pressure-filled environment. It can even be slippery at times. The present invention features a system and method for containment and organization of medical wire.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a system for containment and organization of medical wire. In some embodiments, the system comprises a clamp. In some embodiments, the clamp comprises a shape of a "U". In some embodiments, a first ridged and grooved clamping block is angularly located on a clamp first side posterior end and a second ridged and grooved clamping block is angularly located on a clamp second side posterior end. In some embodiments, the first ridged and grooved clamping block interfaces with the second ridged and grooved clamping block upon closure of the clamp.

In some embodiments, the system comprises a first side compression member. In some embodiments, the first side compression member is located on an inside surface of a clamp first side next to the first ridged and groove clamping block and projects out and away from the clamp first side toward a clamp second side. In some embodiments, the first side compression member comprises a shape of a rectangular prism. In some embodiments, the first side compression member is elastomeric.

In some embodiments, the system comprises a second side compression member. In some embodiments, the second side compression member is located on an inside surface of the clamp second side next to the second ridged and groove clamping block and projects out and away from the clamp second side toward the clamp first side. In some embodiments, the second side compression member comprises a shape of a rectangular prism. In some embodiments, the second side compression member is elastomeric.

In some embodiments, the system comprises an adjustable ratcheting lock located between and attaching the clamp first side and the clamp second side. In some embodiments, a ratcheting lock first end is located on the inside surface of the clamp first side between the clamp first side posterior end and a clamp anterior end and a ratcheting lock second end is located on the inside surface of the clamp second side between the clamp second side posterior end and the clamp anterior end.

In some embodiments, the system comprises a first finger grip located on an outside surface of the clamp first side opposed to the ratcheting lock first end and a second finger grip located on an outside surface of the clamp second side opposed to the ratcheting lock second end.

In some embodiments, medical wire is placed in an open clamp between the first side compression member and the second side compression member. In some embodiments, the clamp is closed having the first ridged and grooved clamping block interlocked against the second ridged and grooved clamping block. In some embodiments, the adjustable ratcheting lock is tightened via manually pinching the clamp via the first finger grip and the second finger grip to compress the first side compression member and the second side compression member against the medical wire for securely holding into position.

DESCRIPTION OF PREFERRED EMBODIMENTS

Figure 1:
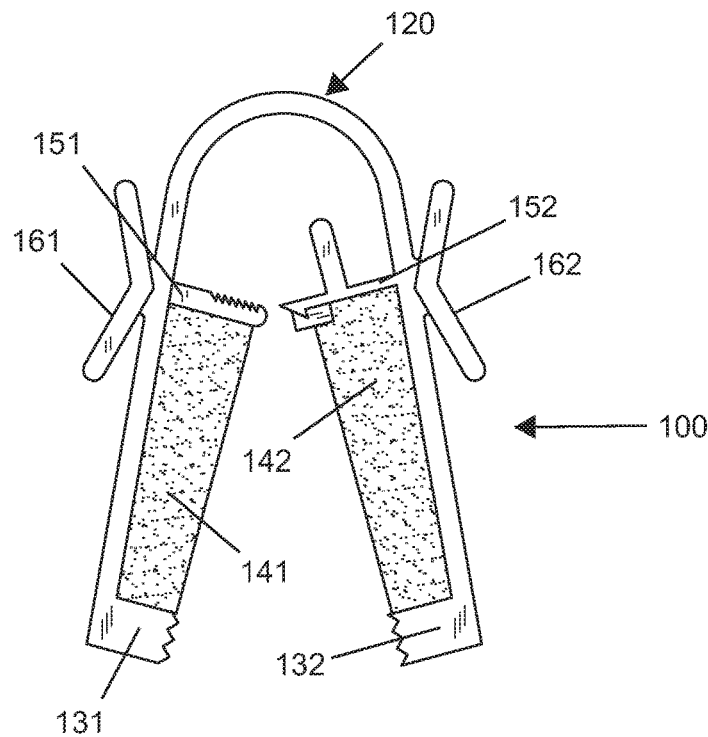
FIG. 1 shows a front view of the present invention, unclamped.
Figure 2:
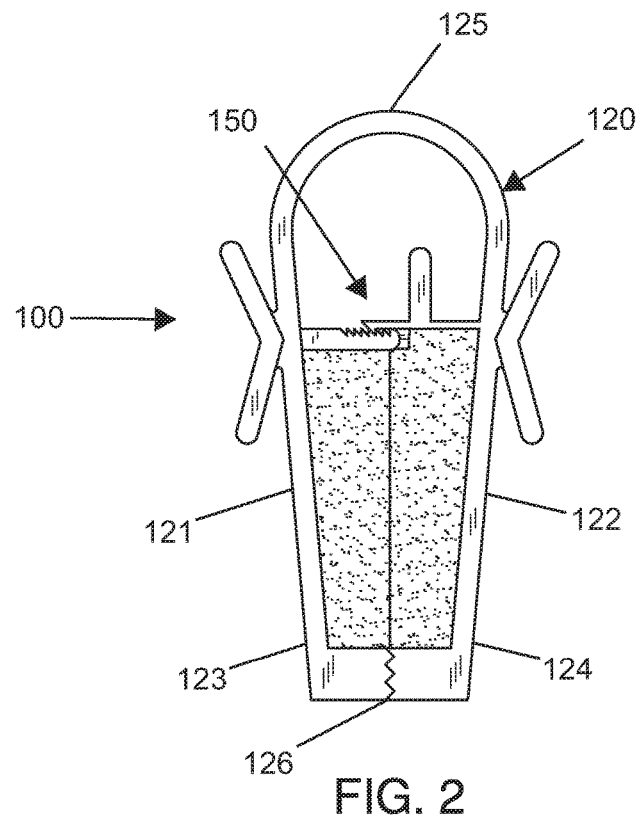
FIG. 2 shows a front view of the present invention, clamped.
Figure 3:
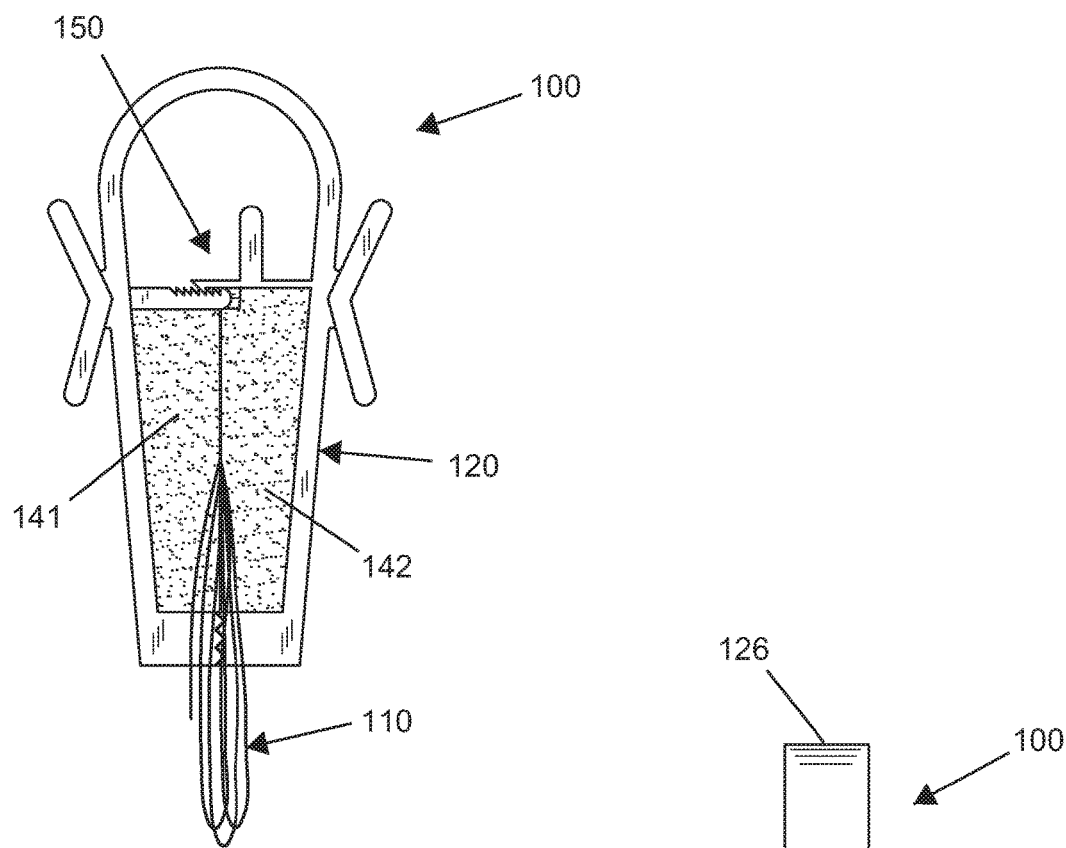
FIG. 3 shows a front view of the present invention, clamped on medical wire.
Figure 4:
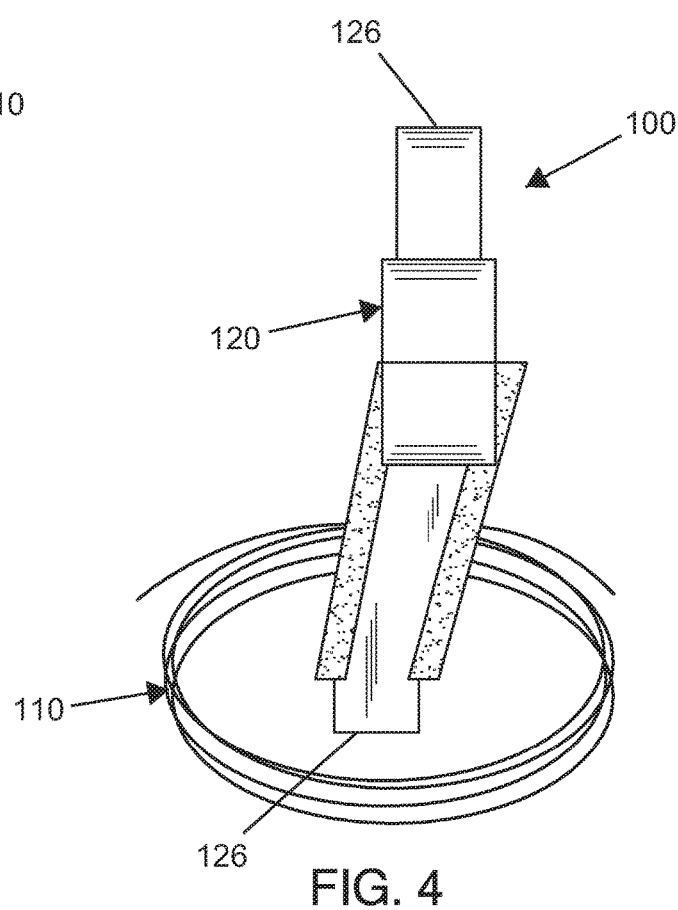
FIG. 4 shows a side view of the present invention, clamped on medical wire.
Figure 5:
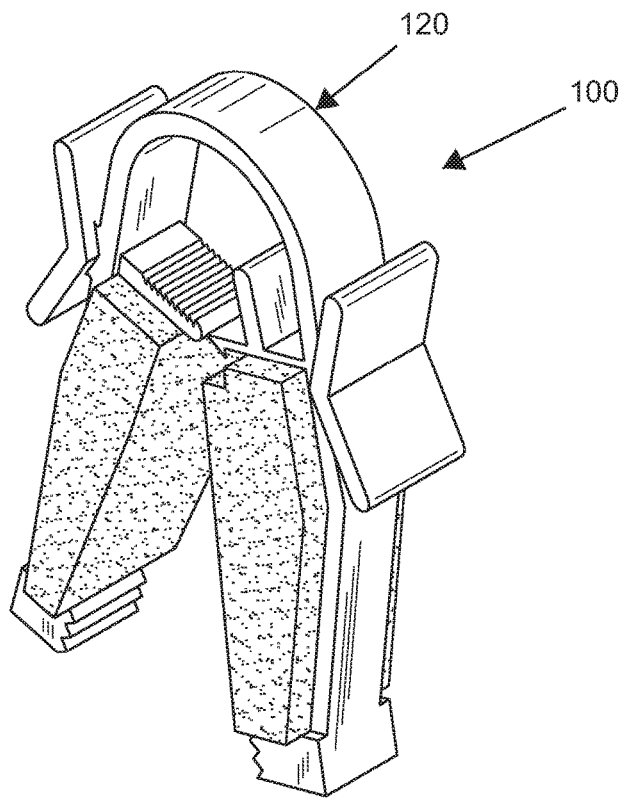
FIG. 5 shows a perspective view of the present invention, unclamped.
Figure 6:
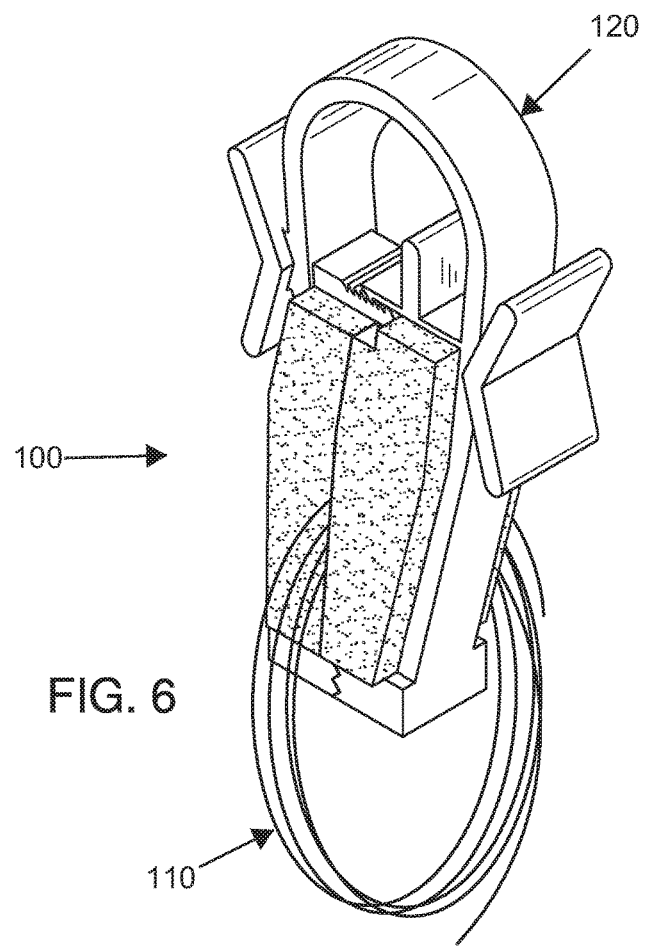
FIG. 6 shows a perspective view of the present invention, clamped on medical wire.

Following is a list of elements corresponding to a particular element referred to herein:

100 Medical wire containment and organization system
110 Medical wire
120 Clamp
121 Clamp first side
122 Clamp second side
123 Clamp first side posterior end
124 Clamp second side posterior end
125 Clamp anterior end
126 Clamp posterior end
131 First ridged and grooved clamping block
132 Second ridged and grooved clamping block
141 First side compression member
142 Second side compression member
150 Ratcheting lock
151 Ratcheting lock first end
152 Ratcheting lock second end
161 First finger grip
162 Second finger grip Referring now to FIG. 1-6, the present invention features a system (100) for containment and organization of medical wire. In some embodiments, the system (100) comprises a clamp (120) having a clamp first side (121), a clamp second side (122), a clamp anterior end (125), and a clamp posterior end (126). In some embodiments, the clamp (120) comprises a shape of a "U". In some embodiments, the clamp (120) comprises a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) is angularly located on the clamp first side posterior end (123) and a second ridged and grooved clamping block (132) is angularly located on the clamp second side posterior end (124). In some embodiments, the first ridged and grooved clamping block (131) mates and interfaces with the second ridged and grooved clamping block (132) upon closure of the clamp (120). In some embodiments, the first ridged and grooved clamping block (131) and the second ridged and grooved clamping block (132) are positioned at a 90 degree angle with respect to the clamp first side (121) and the clamp second side (122), respectively. In some embodiments, the first ridged and grooved clamping block (131) and the second ridged and grooved clamping block (132) are positioned at a 75 degree angle with respect to the clamp first side (121) and the clamp second side (122), respectively. In some embodiments, the first ridged and grooved clamping block (131) and the second ridged and grooved clamping block (132) are positioned at a 60 degree angle with respect to the clamp first side (121) and the clamp second side (122), respectively. In some embodiments, the first ridged and grooved clamping block (131) and the second ridged and grooved clamping block (132) are positioned at a 45 degree angle with respect to the clamp first side (121) and the clamp second side (122), respectively. In some embodiments, the first ridged and grooved clamping block (131) and the second ridged and grooved clamping block (132) are positioned at a 105 degree angle with respect to the clamp first side (121) and the clamp second side (122), respectively. In some embodiments, the first ridged and grooved clamping block (131) and the second ridged and grooved clamping block (132) are positioned at a 120 degree angle with respect to the clamp first side (121) and the clamp second side (122), respectively. In some embodiments, the first ridged and grooved clamping block (131) and the second ridged and grooved clamping block (132) are positioned at a 135 degree angle with respect to the clamp first side (121) and the clamp second side (122), respectively.

In some embodiments, the system (100) comprises a first side compression member (141). In some embodiments, the first side compression member (141) is located on an inside surface of the clamp first side (121) next to the first ridged and grooved clamping block (131) and projects out and away from the clamp first side (121) toward the clamp second side (122). In some embodiments, the first side compression member (141) comprises a shape of a rectangular prism. In some embodiments, the first side compression member (141) is elastomeric.

In some embodiments the first side compression member (141) is constructed of foam. In some embodiments the first side compression member (141) is constructed of rubber. In some embodiments the first side compression member (141) is constructed of latex. In some embodiments the first side compression member (141) comprises a planar interfacing surface.

In some embodiments, the system (100) comprises a second side compression member (142). In some embodiments, the second side compression member (142) is located on an inside surface of the clamp second side (122) next to the second ridged and grooved clamping block (132) and projects out and away from the clamp second side (122) toward the clamp first side (121). In some embodiments, the second side compression member (142) comprises a shape of a rectangular prism. In some embodiments, the second side compression member (142) is elastomeric.

In some embodiments the second side compression member (142) is constructed of foam. In some embodiments the second side compression member (142) is constructed of rubber. In some embodiments the second side compression member (142) is constructed of latex. In some embodiments the second side compression member (142) comprises a planar interfacing surface.

In some embodiments, the system (100) comprises an adjustable ratcheting lock (150) located between and attaching the clamp first side (121) and the clamp second side (122) in a releasable manner. In some embodiments, a ratcheting lock first end (151) is located on the inside surface of the clamp first side (121) between the clamp first side posterior end (123) and the clamp anterior end (125) and a ratcheting lock second end (152) is located on the inside surface of the clamp second side (122) between the clamp second side posterior end (124) and the clamp anterior end (125). In some embodiments, the adjustable ratcheting lock (150) comprises a plurality of settings corresponding to a level of compression between the first side compression member (141) and the second side compression member (142).

In some embodiments, the system (100) comprises a first finger grip (161) located on an outside surface of the clamp first side (121) opposed to the ratcheting lock first end (151) and a second finger grip (162) located on an outside surface of the clamp second side (122) opposed to the ratcheting lock second end (152).

In some embodiments, medical wire (110) is placed in an open clamp (120) between the first side compression member (141) and the second side compression member (142). In some embodiments, the clamp (120) is closed having the first ridged and grooved clamping block (131) interfacing and interlocked against the second ridged and grooved clamping block (132). In some embodiments, the adjustable ratcheting lock (150) is tightened via manually pinching the clamp (120) via the first finger grip (161) and the second finger grip (162) to compress the first side compression member (141) and the second side compression member (142) against the medical wire (110) for securely holding into position.

In some embodiments, the first side compression member (141) is located on the inside surface of the clamp first side (121) and the second side compression member (142) is located on the inside surface of the clamp second side (122) via a water resistant adhesive.

In some embodiments, the first side compression member (141) is located on the inside surface of the clamp first side (121) and the second side compression member (142) is located on the inside surface of the clamp second side (122) via a saline compatible adhesive.

In some embodiments, the first side compression member (141) is located on the inside surface of the clamp first side (121) and the second side compression member (142) is located on the inside surface of the clamp second side (122) via mechanical fastening.

In some embodiments, the system (100) further comprises medical wire (110).

In some embodiments, the medical wire (110) is interventional procedure wire.

In some embodiments, the medical wire (110) is cardiac catheterizing wire.

In some embodiments, the medical wire (110) is hydrophilic wire.

In some embodiments, the medical wire (110) is micro wire.

In some embodiments, the medical wire (110) is guide wire.

In some embodiments, the medical wire (110) is a catheter.

In some embodiments, the system (100) further comprises a catheter and guide wire bowl. In some embodiments, the system (100) further comprises a bowl.

In some embodiments, the system (100) further comprises a plurality of clamps (120). In some embodiments, the system (100) further comprises a plurality of color coded clamps (120). In some embodiments, the system (100) further comprises a plurality of labeled clamps (120).

In some embodiments, the system (100) further comprises an indicator located on each clamp (120) for indicating wire type or size.

In some embodiments, the indicator is a unique color.

A method of containment and organization of medical wire comprises obtaining a system (100) for containment and organization of medical wire comprising a clamp (120) having a clamp first side (121), a clamp second side (122), a clamp anterior end (125), and a clamp posterior end (126). In some embodiments, the clamp (120) comprises a shape of a "U". In some embodiments, the clamp (120) comprises a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) is angularly located on the clamp first side posterior end (123) and a second ridged and grooved clamping block (132) is angularly located on the clamp second side posterior end (124). In some embodiments, the first ridged and grooved clamping block (131) mates with and interfaces with the second ridged and grooved clamping block (132) upon closure of the clamp (120). In some embodiments, the system (100) comprises a first side compression member (141). In some embodiments, the first side compression member (141) is located on an inside surface of the clamp first side (121) next to the first ridged and grooved clamping block (131) and projects out and away from the clamp first side (121) toward the clamp second side (122). In some embodiments, the first side compression member (141) comprises a shape of a rectangular prism. In some embodiments, the first side compression member (141) is elastomeric. In some embodiments, the system (100) comprises a second side compression member (142). In some embodiments, the second side compression member (142) is located on an inside surface of the clamp second side (122) next to the second ridged and grooved clamping block (132) and projects out and away from the clamp second side (122) toward the clamp first side (121). In some embodiments, the second side compression member (142) comprises a shape of a rectangular prism. In some embodiments, the second side compression member (142) is elastomeric. In some embodiments, the system (100) comprises an adjustable ratcheting lock (150) located between and releasably attaching the clamp first side (121) and the clamp second side (122). In some embodiments, a ratcheting lock first end (151) is located on the inside surface of the clamp first side (121) between the clamp first side posterior end (123) and the clamp anterior end (125) and a ratcheting lock second end (152) is located on the inside surface of the clamp second side (122) between the clamp second side posterior end (124) and the clamp anterior end (125). In some embodiments, the system (100) comprises a first finger grip (161) located on an outside surface of the clamp first side (121) opposed to the ratcheting lock first end (151) and a second finger grip (162) located on an outside surface of the clamp second side (122) opposed to the ratcheting lock second end (152). In some embodiments, the system (100) comprises medical wire (110). In some embodiments, the system (100) comprises a catheter and guide wire bowl.

In some embodiments, the method comprises removing the medical wire (110) from its sterile packaging.

In some embodiments, the method comprises placing medical wire (110) in an open clamp (120) between the first side compression member (141) and the second side compression member (142) in either a straight or a looped position having at least one strand of the medical wire (110) in contact with the first side compression member (141) and the second side compression member (142).

In some embodiments, the method comprises closing the clamp (120) with the first ridged and grooved clamping block (131) interfacingly interlocked against the second ridged and grooved clamping block (132).

In some embodiments, the method comprises tightening the clamp (120) with the adjustable ratcheting lock (150) via manually pinching the clamp (120) via the first finger grip (161) and the second finger grip (162) to compress the first side compression member (141) and the second side compression member (142) against the medical wire (110) for securely holding into position.

In some embodiments, the method comprises placing the clamp (120) with the medical wire (110) into the catheter and guide wire bowl in preparation for use.

In some embodiments, the method comprises discarding the clamp (120) after a single use.

In some embodiments, the method comprises a plurality of clamps (120) used with a plurality of medical wires (110). In some embodiments, the plurality of clamps (120) comprise a unique indicator located on each clamp (120) for indicating wire type or size.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system for containment and organization of medical wire, wherein the system comprises:
   a clamp having a first side, a second side, an anterior portion, a posterior end, a first side posterior portion, and a second side posterior portion, wherein the first side and second side are joined at the anterior portion, and wherein the clamp is movable between an open configuration and a closed configuration;
   a locking mechanism configured to retain the clamp in the closed configuration;
   a first compression member disposed on an inside surface of the first side posterior portion, wherein the first compression member is elastomeric; and
   a second compression member disposed on an inside surface of the second side posterior portion, wherein the second compression member is elastomeric;
   wherein the clamp is configured to receive medical wire between the first compression member and the second compression member such that, when the clamp is moved to the closed configuration, the first compression member and the second compression member are compressed against the medical wire to secure a position of the medical wire within the clamp.

2. The system of claim 1, wherein the locking mechanism extends between the first side and second side of the clamp.

3. The system of claim 2, wherein the locking mechanism comprises a ratchet first portion extending from first side of the clamp and a ratchet second portion extending from the second side of the clamp, and wherein the ratchet first portion and ratchet second portion are configured such that relative movement between the ratchet first portion and ratchet second portion is limited when the ratchet first portion contacts the ratchet second portion.

4. The system of claim 2, wherein the locking mechanism comprises a plurality of settings corresponding to a plurality of states of compression between the first compression member and the second compression member at which the clamp may be maintained.

5. The system of claim 1, further comprising a first clamping block extending from the first side posterior portion and arranged closer to the posterior end of the clamp than the first compression member, and a second clamping block extending from the second side posterior portion and arranged closer to the posterior end of the clamp than the second compression member.

6. The system of claim 5, wherein the first clamping block is configured to contact the second clamping block while the clamp is in the closed configuration.

7. The system of claim 5, wherein the first clamping block comprises a ridged and grooved surface which is configured to interface with a ridged and grooved surface on the second clamping block.

8. The system of claim 1, wherein the first compression member comprises a planar interfacing surface configured to contact a planar interfacing surface of the second compression member when the clamp is in the closed configuration.

9. The system of claim 1, wherein the first compression member and the second compression member each comprise a rectangular prism.

10. The system of claim 1, wherein the anterior portion is arranged in a first plane, and wherein the first side posterior portion and second side posterior portion are angularly offset from the first plane.

11. The system of claim 10, wherein the first compression member and the second compression member each comprise a rhombic prism.

12. The system of claim 10, wherein at least one of the first compression member and the second compression member is fastened to the clamp via a water resistant adhesive.

13. The system of claim 1, further comprising a first finger recess disposed on the first side of the clamp and a second finger recess disposed on the second side of the clamp, the clamp being configured such that force applied by one of the first finger recess and the second finger recess against the other of the first finger recess and the second finger recess increases an amount of compression of the first compression member and the second compression member.

14. A method of containment and organization of medical wire with a clamp, the clamp comprising a first side, a second side, an anterior portion, and a posterior end, wherein the first side and second side are joined at the anterior portion, the method comprising;
   placing medical wire between a first compression member disposed on an inside surface of the first side of the clamp and a second compression member disposed on an inside surface of the clamp, wherein the first compression member and the second compression member are elastomeric;
   moving the clamp from an open configuration to a closed configuration, such that the first compression member and the second compression member are compressed against the medical wire to secure to a position of the medical wire within the clamp; and
   operating a locking mechanism extending between the first side and second side of the clamp such that the clamp is maintained in the closed configuration.

15. The method of claim 14, further comprising adjusting a ratchet on the locking mechanism such that the first compression member and second compression member are further compressed against the medical wire.

16. The method of claim 15, wherein adjusting the ratchet such that the first compression member and second compression member are further compressed against the medical wire comprises pinching the first side against the second side of the clamp.

17. The method of claim 14, further comprising adjusting a ratchet on the locking mechanism such that the first compression member and second compression member are less compressed against the medical wire.

18. The method of claim 17, wherein adjusting the ratchet such that the first compression member and second compression member are less compressed against the medical wire comprises:
   decoupling a ratchet first end extending from the first side of the clamp from a ratchet second end extending from the second side of the clamp;

moving the ratchet from a first position to a second position by moving the ratchet first end with respect to the ratchet second end; and coupling the ratchet first end to the ratchet second end.

19. The method of claim 14, further comprising releasing the locking mechanism.

20. The method of claim 19, wherein the clamp is biased toward the open configuration such that, after releasing the locking mechanism, the clamp moves to the open configuration.

* * * * *